United States Patent
Shigeyuki et al.

(10) Patent No.: US 6,287,587 B2
(45) Date of Patent: *Sep. 11, 2001

(54) PROCESS FOR PRODUCING SUSTAINED-RELEASE PREPARATION BY IN-WATER DRYING

(75) Inventors: Takada Shigeyuki, Hyogo; Taira Keiko, Osaka; Iwasa Susumu, Kyoto, all of (JP)

(73) Assignee: Takeda Chemical Industries, Ltd., Osaka (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/112,317
(22) Filed: Jul. 9, 1998
(30) Foreign Application Priority Data Jul. 15, 1997 (JP) .................................................. 9-190300

(51) Int. Cl.[7] .................................................. A61F 2/00
(52) U.S. Cl. .......................... 424/426; 424/451; 424/452; 424/457; 514/937; 514/938; 514/962; 514/963; 514/2
(58) Field of Search .................................. 424/426, 451, 424/452, 457; 514/937, 938, 962, 963, 2

(56) References Cited

U.S. PATENT DOCUMENTS

| | | | |
|---|---|---|---|
| 4,954,298 | * 9/1990 | Yamamoto et al. | 264/4.6 |
| 5,271,945 | * 12/1993 | Yoshioka et al. | 424/489 |
| 5,622,657 | 4/1997 | Takada et al. | 264/4.32 |
| 5,651,990 | * 7/1997 | Takada et al. | 424/497 |
| 5,876,756 | 3/1999 | Takada et al. | 424/489 |

FOREIGN PATENT DOCUMENTS

| | | |
|---|---|---|
| 709 085 | 5/1996 | (EP) . |
| 0709085 | * 5/1996 | (EP) . |
| 709085 A1 | * 5/1996 | (EP) . |
| 0765660 | * 4/1997 | (EP) . |
| 765660 A2 | * 4/1997 | (EP) . |
| 765 660 | 4/1997 | (EP) . |
| 765660 | * 4/1997 | (EP) . |
| 063613 | 4/1986 | (JP) . |
| WO 96/07399 | 3/1996 | (WO) . |
| WO97/35563 | 10/1997 | (WO) . |

* cited by examiner

Primary Examiner—Thurman K. Page
Assistant Examiner—Lakshmi S. Channavajjala
(74) Attorney, Agent, or Firm—Fitzpatrick, Cella, Harper & Scinto

(57) ABSTRACT

The present invention is to provide sustained-release microcapsules which contains high amount of a drug, suppresses initial release and shows stable release, and the production method of which comprises adding a physiologically active substance to biodegradable polymer in an organic solvent containing a fat and oil (in particular, vitamin E) and dispersing and emulsifying the mixture.

14 Claims, 2 Drawing Sheets

PROCESS FOR PRODUCING SUSTAINED-RELEASE PREPARATION BY IN-WATER DRYING

FIELD OF THE INVENTION

The present invention relates to a sustained-release microcapsule which suppresses initial release of an excess amount of a physiologically active substance right after administration of the microcapsule and releases stably a constant amount of the physiologically active substance for a long time from right after administration of the microcapsule, and a production method thereof.

BACKGROUND OF THE INVENTION

On sustained-release microcapsules of various physiologically active polypeptides or low molecular water-soluble drugs, many reports have been made [Critical Reviews in Therapeutic Drug Carrier Systems, 12, 1–9 (1995); JP-A H2(1990)2-503315; EP-A-0586238; J. Pharm. Sci., 75, 750–755 (1986); JP-A S57(1987)-118512]. Most of the microcapsules so far reported have the following drawbacks:

(1) in the manufacturing process, the amount of the water-soluble drug leaked to the outer aqueous phase is relatively large to invite a relatively low entrapment ratio of the drug, (2) the resulting microcapsules are generally porous and cause a relatively large initial release, and (3) in the manufacturing process, the physiologically active substance is denatured to invite insufficient bioavailability. Thus, at the present stage, sustained release of the drug over a desirable long period have not yet been succeeded.

In JP-A S61(1986)-63613, improvement of sustained release of microspheres was reported. That is, there is described that for the purpose of preventing decrease of release rate of the active ingredient a certain hour after administration of microspheres whose base is polylactic acid, in an organic solvent of polylactic acid to which the active ingredient is dispersed, an oil soluble additive (medium chain fatty acid triglyceride, a lower fatty acid triglyceride, etc.) which is soluble in said solvent and which is biodegradable is uniformly dissolved. However, there is no suggestion on application to the other bases nor on preparation of microcapsules using a solution of the active ingredient.

In JP-A H8(1996)-151321 [EP-A-0709085], there is disclosed microcapsules which contains an amorphous type water-soluble physiologically active substance and polymer, and which are produced from a S/O/W type emulsion. However, there is no description on a process for producing microcapsules using a solution of a drug as an inner aqueous phase nor on a method using metal complex of a water-soluble physiologically active peptide.

In EP 0765660, there is disclosed microcapsules which contains an amorphous type 2-piperazinone-1-acetic acid derivative, and in a production method thereof, a S/O/W type emulsion is employed. However, there is no description on a process for producing microcapsules using a solution of a drug as an inner aqueous phase nor on a method using metal complex of a water-soluble physiologically active peptide.

In general, in a process for producing microcapsules of a water-soluble physiologically active substance, it is more advantageous to employ a W/O type emulsion than a S/O type emulsion where the drug is used as solid substances in view of equivalency of drug content or operation, and it is desired to employ a W/O type emulsion in an industrial manufacture with large scale.

OBJECT OF THE INVENTION

It is preferable for sustained-release preparations using biodegradable polymers to suppress initial release of an excess amount of a physiologically active substance, in particular release of an excess amount of the same within one day after administration thereof, and to releases stably a constant amount of the physiologically active substance for a long time. The present invention is to provide a simple and convenient process for producing uniform sustained-release microcapsules which maintain physiological activity of the physiologically active substance, suppress initial release, and release stably a constant amount of the physiologically active substance.

SUMMARY OF THE INVENTION

The present invention have intensively studied to solve the above problems and, as a result, have found that in a process for producing sustained-release microcapsules of a water-soluble physiologically active substance, it is possible to produce very useful sustained-release microcapsules which suppress initial release of an excess amount of the physiologically active substance right after administration and release stably a constant amount of the physiologically active substance for a long time, by adding about 3% to about 30% of a fat and oil to an organic solvent solution of said biodegradable polymer and using the thus obtained uniform solution as an oil phase. Further diligent studies based on this finding have reached the accomplishment of the present invention.

The present invention relates to (1) A process for producing a sustained-release microcapsule of a water-soluble physiologically active substance, which comprises forming a w/o type emulsion comprising a solution containing a water-soluble physiologically active substance as an inner aqueous phase and an uniform organic solvent solution containing (i) a biodegradable polymer and (ii) a "fat and oil" as an oil phase, and removing the organic solvent;

(2) A process as described in the above (1), wherein the w/o type emulsion is dispersed in an aqueous phase, and the organic solvent is removed by in-water drying;

(3) A process as described in the above (1), wherein the inner aqueous phase is a solution containing a water-soluble physiologically active substance and a basic substance;

(4) A process as described in the above (1), wherein the water-soluble physiologically active substance is a polypeptide the molecular weight of which ranges from about 200 to about 80,000;

(5) A process as described in the above (1), wherein the water-soluble physiologically active substance is an integrin antagonist;

(6) A process as described in the above (5), wherein the integrin antagonist is a GPIIb/IIIa antagonist;

(7) A process as described in the above (6), wherein the GPIIb/IIIa antagonist is a 2-piperazinone-1-acetic acid derivative represented by the formula (I):

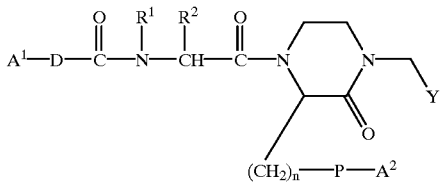

wherein $A^1$ and $A^2$ are independently a proton-accepting group or a group convertible into a proton-accepting group, D is a spacer having a 2- to 6-atomic chain optionally bonded through a hetero atom and/or a 5- or 6-membered ring (provided that the 5- or 6-membered ring is counted as 2- or 3-atomic chain, depending on its bonding position), $R^1$ is a hydrogen atom or hydrocarbon group, $R^2$ is a hydrogen atom or a residual group formed by removing —CH(NH$_2$)COOH from an α-amino acid, or $R^1$ and $R^2$ may be combined to form a 5- or 6-membered ring, P is a spacer having a 1- to 10-atomic chain optionally bonded through a hetero atom and/or a 5- or 6-membered ring (provided that the 5- or 6-membered ring is counted as 2- or 3-atomic chain, depending on its bonding position), Y is an optionally esterified or amidated carboxyl group, and n is an integer of 0–8; or a salt thereof;

(8) A process as described in the above (7), wherein the 2-piperazinone-1-acetic acid derivative (I) is (S)-4-(4-guanidinobenzoylamino)acetyl-3-[3-(4-guanidinobenzoylamino)]propyl-2-oxopiperazine-1-acetic acid or a salt thereof;

(9) A process as described in the above (7), wherein the 2-piperazinone-1-acetic acid derivative (I) is (S)-4-(4-guanidinobenzoylamino)acetyl-3-[3-(4-guanidinobenzoylamino)]propyl-2-oxopiperazine-1-acetic acid hydrochloride;

(10) A process as described in the above (7), wherein the 2-piperazinone-1-acetic acid derivative (I) is (S)-4-(4-guanidinobenzoylamino)acetyl-3-[3-(4-guanidinobenzoylamino)]propyl-2-oxopiperazine-1-acetic acid dihydrochloride;

(11) A process as described in the above (1), wherein the biodegradable polymer is an aliphatic polyester;

(12) A process as described in the above (11), wherein the aliphatic polyester is a lactic acid/glycolic acid copolymer;

(13) A process as described in the above (1), wherein the fat and oil is an oil soluble vitamin;

(14) A process as described in the above (13), wherein the oil soluble vitamin is α-tocopherol;

(15) A process as described in the above (1), wherein the final concentration of the fat and oil in a whole content of the sustained-release microcapsule is about 3% to about 30% (w/w);

(16) A process as described in the above (1), wherein the W/O type emulsion comprising a solution containing a water-soluble physiologically active substance and a basic substance as an inner aqueous phase and an uniform organic solvent solution containing a biodegradable polymer and a fat and oil as an oil phase is dispersed in an aqueous phase to form a W/O/W type emulsion, and the organic solvent is removed by in-water drying;

(17) A process as described in the above (3) or (16), wherein the basic substance is a basic amino acid;

(18) A process as described in the above (17), wherein the basic amino acid is L-arginine;

(19) A process as described in the above (3) or (16), wherein the final concentration of the basic substance in a whole content of the sustained-release microcapsule is about 1% to about 8% (w/w);

(20) A process for producing a sustained-release microcapsule, which comprises removing an organic solvent from a S/O type dispersion where a metal complex of a water-soluble physiologically active peptide is dispersed in an uniform organic solvent solution containing a biodegradable polymer and a fat and oil;

(21) A process as described in the above (20), wherein the S/O type dispersion is dispersed in an aqueous phase to form a S/O/W type emulsion, and the organic solvent is removed by in-water drying;

(22) A process as described in the above (20), wherein the water-soluble physiologically active peptide is human growth hormone;

(23) A process as described in the above (20), wherein the metal complex of the water-soluble physiologically active peptide is a zinc complex of human growth hormone.;

(24) A sustained-release microcapsule produced by the process according to the above (1);

(25) A sustained-release microcapsule produced by the process according to the above (20);

(26) Use of a fat and oil for the manufacture of a sustained-release microcapsule of a water-soluble physiologically active substance, said microcapsule being produced by forming a w/o type emulsion comprising a solution containing the water-soluble physiologically active substance as an inner aqueous phase and an organic solvent solution containing a biodegradable polymer as an oil phase, and removing the organic solvent;

(27) Use of a fat and oil for the manufacture of a sustained-release microcapsule of a metal complex of a water-soluble physiologically active peptide; etc.

DETAILED DESCRIPTION OF THE INVENTION

Figure 1:
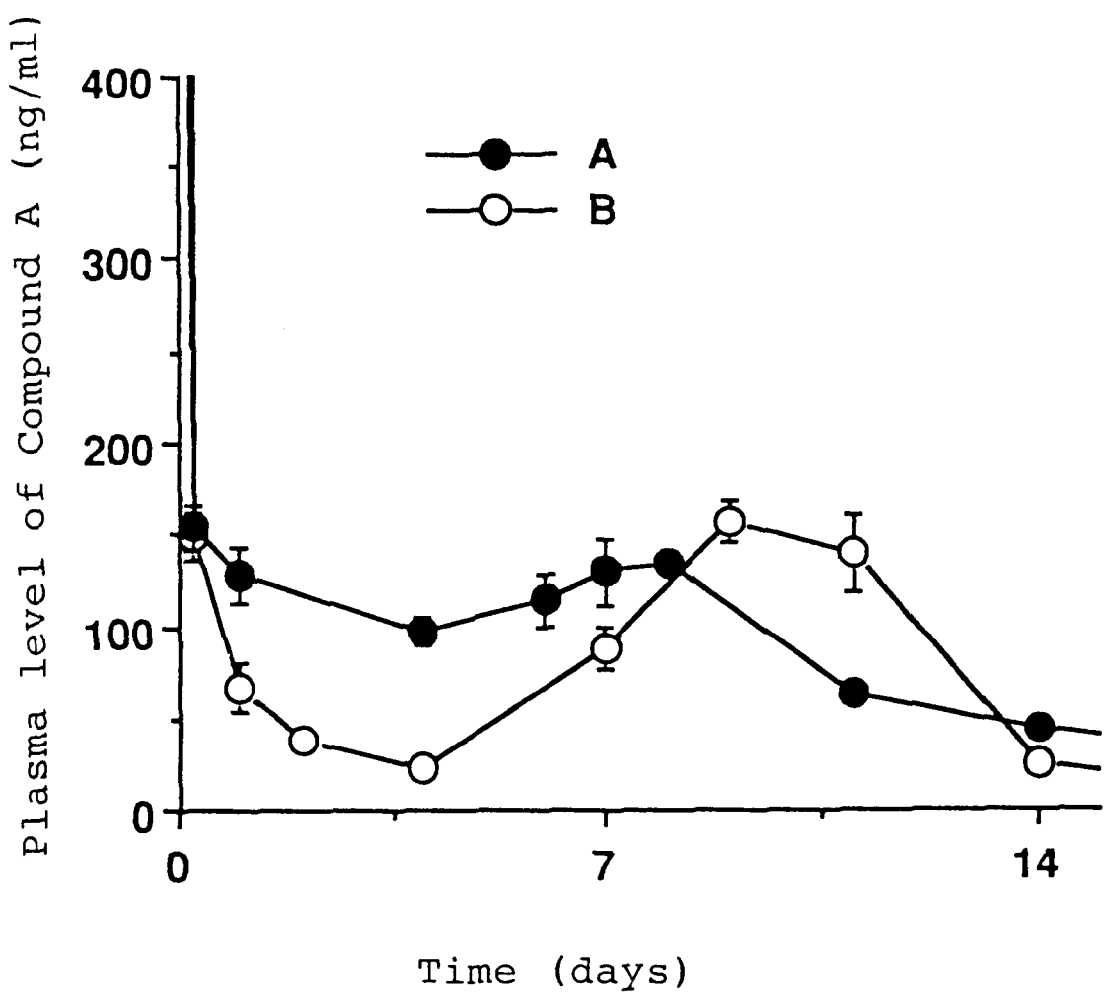
FIG. 1 shows the time-course changes of the plasma level of the drug after administration of the microcapsules used in Test Example 1.

The abbreviations of amino acid, peptide, protecting group, etc. in this specification are based on those established by IUPAC-IUB Commission on Biochemical Nomenclature or those commonly used in the relevant fields. When optical isomers of amino acids are present, they are L-isomers unless otherwise specified. The term "microcapsule" used in this specification includes microspheres, microcapsules, microparticles, nanoparticles, nanospheres, nanocapsules, etc. which contain a physiologically active substance and a polymer.

The term "S/O/W type emulsion" and "W/O/W type emulsion" used in this specification means a solid/oil/water (solid phase in oil in water) type emulsion and a water/oil/water (water phase in oil in water) type emulsion, respectively.

Examples of the water-soluble physiologically active substances include any water-soluble drugs such as a physiologically active polypeptide; a compound used as anti-platelet aggregation agents (e.g. integrin antagonist), anti-tumor agents, antibiotics, antipyretics, analgesics, anti-inflammatory agents, antitussive expectorants, sedatives, muscle relaxants, antiepileptic agents, antiulcer agents, antidepressants, antiallergic agents, cardiotonics, antiarrhythmic agents, vasodilators, hypotensive agents, diuretics, antidiabetic agents, anticoagulants, hemostatics, antituberculous agents, hormone preparations, narcotic antagonists, bone resorption inhibitors, osteogenesis promoting agents, angiogenesis inhibitors, etc.; etc.

Examples of said water-soluble physiologically active substances include physiologically active substances whose water-solubility at 25° C. is not less than 0.1% (w/w), preferably not less than 1% (w/w).

The physiologically active polypeptide as a component of the present invention is exemplified by various peptides or proteins that possess physiologically activity beneficial to mammals and that can be used clinically. Said "physiologically active polypeptide" has a molecular weight of, for example, about 200 to about 200,000, calculated on a monomer basis, preferably about 200 to about 80,000. Preferred physiologically active polypeptides include polymers classified in the biological field as proteins having higher structure. Any kind of physiologically active polypeptides can be used for the present invention, as long as the object of the present invention is accomplished. Typical examples include growth factors, cytokines, enzymes, hormones, etc. More specifically, the following peptides and protein may be mentioned as examples:

(1) Examples of the growth factors include nerve growth factor (NGF-1, NGF-1, etc.), nerve trophic factor (NTF), epidermal growth factor (EGF), platelet-derived growth factor(PDGF), insulin-like growth factor (IGF-1, IGF-2, IGF-3, etc.), fibroblast growth factor (aFGF, bFGF), osteogen growth factor (BMP-1, BMP-2, BMP-3, BMP-4, etc.), atrial natriuretic factor (ANP), cartilage induction factor, etc.

(2) Examples of the cytokines include interferon (IFN-α, IFN-β, IFN-γ, etc.), interleukin (IL-1 to IL-11, etc.), cachectin, oncostatin, colony-stimulating factor (G-CSF, M-CSF, GM-CSF, etc.), trombopoietin (TPO), erythropoietin (EPO), etc.

(3) Examples of the enzymes include tissue plasminogen activator (tPA), urokinase (UK), streptokinase, protein C, metalloprotease, superoxide disumutase (SOD), Factor VIII and IX, etc.

(4) Examples of the hormones include growth hormone (GH), growth hormone-releasing factor(GRF), insulin, glucagon, gastrin, prolactin, adrenocorticotrophic hormone (ACTH), thyroid-stimulatinghormone (TSH), follicle-stimulatinghormone (FSH), luteinizing hormone (LH), human chorionic gonadotropin (HCG), calcitonin, etc.

Preferable examples of said physiologically active polypeptide include hormones [e.g. growth hormone (human growth hormone, etc.), insulin (human insulin, etc.), etc.], cytokines (e.g. interferon, interleukin, etc.), etc.

The physiologically active polypeptide for the present invention include polypeptides naturally derived and synthesized, semi-synthesized or recombinant polypeptides produced by gene recombination or peptide synthesis [e.g. recombinant human growth hormone (hereinafter, referred to as rhGH)]. Such polypeptide may have a sugar chain, and the structure of said sugar chain may be different from that of natural polypeptide. Also, they include muteins, derivatives, analogues, active fragments, etc. of the physiologically active polypeptide or protein. Hereinafter, the terms "physiologically active polypeptide", "growth hormones", "insulins", "interferons" and "interleukins" are to be understood to include respectively those having a sugar chain and their muteins, derivatives, analogues and active fragments. When the physiologically active polypeptide is muteins, derivatives or analogues of an optional polypeptide, its mechanism of action may be either agonistic or antagonistic.

The physiologically active polypeptide for the present invention may be in a form of complex with a metal atom. Examples of the metal complex of the polypeptide include a water insoluble (or hardly soluble) polyvalent metal complex, metal salt, etc. of the polypeptide. Any metal may be used for the metal complex without limitation, as long as it is a metal that does not adversely affect the living body. For example, a water-soluble polyvalent metal (divalent, trivalent or tetravalent metal, e.g. transition metal such as iron, copper, zinc, etc., IIIb group metal such as aluminum, etc., Ivb group metal such as tin, etc.) is preferably used.

Examples of the metal complex of the polypeptides include physiologically active polypeptide metal salts obtained by contacting a physiologically active polypeptide with a water-soluble polyvalent metal salt (e.g. a salt of the above polyvalent metal with an inorganic acid such as hydrochloric acid, sulfuric acid, nitric acid, thiocyanic acid, etc. or a salt of the above polyvalent metal with an organic acid such as aliphatic carboxylic acid (e.g. aliphatic mono-, di- or tri-carboxylic acid, preferably, aliphatic carboxylic acid having 2–9 carbon atoms, etc.), aromatic acid (e.g. benzoic acid, salicylic acid, etc.), etc.). Said physiologically active peptide metal salt can be produced by mixing a physiologically active polypeptide with a water-soluble polyvalent metal salt in a solution whose pH is selected from the scope where solubility of both the reactants is not extremely decreased.

Examples of ratio (mole ratio) of the physiologically active polypeptide and the water-soluble polyvalent metal salt include 1:1 to 1:1000, preferably 1:1 to 1:100, more preferably 1:1 to 1:50. It is preferable to employ concentration of both of the reactants which is within the range of solubility of respective reactant and which is over the range of solubility of the resulting complex. If necessary, the solution to be employed may be adjusted to a weakly acidic, neutral or weakly basic solution.

When the physiologically active polypeptide have an acidic group (e.g. carboxyl group, sulfo group, etc.), it is advantageous to use its water-insoluble complex (or complex which is hardly soluble in water) with a polyvalent metal for the purpose of improvement of entrapment into microcapsule and control of release.

Examples of the anti-platelet aggregation agents include integrin antagonists, in particular, GPIIb/IIIa antagonists. Examples of the GPIIb/IIIa antagonists include snake venom peptide (e.g. barbourin, or peptides having amino acid sequence: Arg-Gly-Asp such as Arg-Gly-Asp-Ser, (Arg-Gly-Asp-Ser)tetramer, Gly-Arg-Gly-Asp-Ser-Pro, cyclo-S, S-[AC-Cys(N α-methyl)Arg-Gly-D-Asn-penicillamine]-NH$_2$ (SK&F-106760: Pharm. Res., 11, 1358–1390, 1994), andacompoundhaving an activity similar to GPIIb/IIIa antagonistic activity such as (S)-4-[(4-amidinobenzoyl) glycyl]-3-methoxy-carbonyl-methyl-2-oxopiperazine-1-acetic acid, 4-(4-amidinobenzoyl-glycyl)-2-oxopiperazine-1,3-2-acetic acid hydrochloride, L-Tyr-N-(butylsulfonyl)-O-[4-(4-piperidinyl)butyl]monohydrochloride (L-700462/MK-383: Circulation, 88, 1512–1517, 1993), ethyl 3S-[4-[[4-(aminoiminomethyl)phenyl]amino]-1,4-dioxobutyl] amino-4-pentinoate hydrochloride (SC-54684A: Circulation, 91, 403–410, 1995), [1-[N-(P-amidinophenyl)-L-Tyr]-4-piperidinyl]acetic acid (Ro-44-9883: Thromb. Haemostas., 70, 817–821, 1993), cyclic[D-2-aminobutyryl-N-2-methyl-L-Arg-Gly-L-Asp-3-aminomethyl-benzoic acid]methane sulfonate (DMP728: Circulation, 89, 3–12, 1994), (3S-trans)-5-[[[4'-(aminoiminomethyl)-[1,1'-biphenyl]-4-yl]oxy]-methyl]-2-oxo-pyrrolidine-3-acetic acid (Fradaf iban; BIBU 52: Circulation, 96, 1130–1138, 1997) represented by the formula:

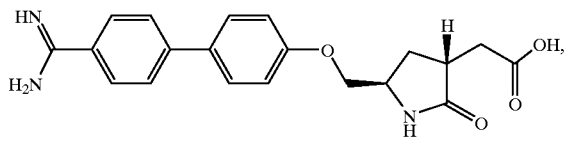

2(S)-[(p-toluenesulfonyl)amino]-3-[[[5,6,7,8-tetrahydro-4-oxo-5-[2-(piperidin-4-yl)ethyl]-4H-pyrazoro [1,5-a][1,4]-diazepin-2-yl]carbonyl]amino]propionic acid (L-738,167: The Journal of Pharmacology and Experimental Therapeutics, 281, 677–689, 1997), Intrifiban (Integrelin) (Circulation, 94, 2083–2089, 1996) represented by the formula:

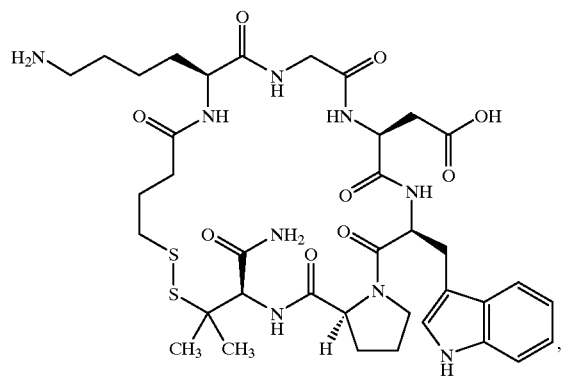

FK-633 (JP-A H5(1993)-148207) represented by the formula:

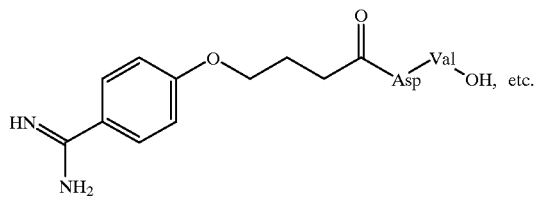

Further examples of the GPIIb/IIIa antagonists include 2-piperazinone-1-acetic acid derivative (I) represented by the above formula (I) or a salt thereof, etc. Moreover, preferred examples of the 2-piperazinone-1-acetic acid derivative include those described in WO96/33982 and, in particular, the 2-piperazinone-1-acetic acid derivative (I) represented by the above formula (I) wherein $A^1$ and $A^2$ are independently (1) an amidino group or a guanidino group, each of which may be substituted with a $C_{2-8}$ alkoxycarbonyloxy group or a $C_{2-8}$ alkoxycarbonyl group, (2) an amino group optionally having an oxadiazolyl group which may be substituted with a substituent selected form an oxo group and an optionally halogenated $C_{1-4}$ alkyl group, or (3) an oxadiazolyl group which may be substituted with a substituent selected from an oxo group and an optionally halogenated $C_{1-4}$ alkyl group [preferably, (1) an amidino group or a guanidino group, each of which may be substituted with a methoxycarbonyloxy group or (2) an amino group optionally having a substituent selected from a 5-oxo-1,2,4-oxadiazol-3-yl group and a 5-trifluoromethyl-1,2,4-oxadiazol-3-yl group]; D is a group of the formula:

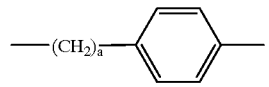

(wherein a is an integer of 0–2) [preferably, a phenylene group]; $R^1$ is a hydrogen atom; $R^2$ is a hydrogen atom or a $C_{1-4}$ alkyl group optionally having a phenyl group which may be substituted with a $C_{1-4}$ alkoxy group [preferably, a hydrogen atom or a p-methoxybenzyl group]; P is a group of the formula: —Z—B— (wherein Z is a chemical bond, —NH— or —NH—CO— and B is a group of the formula:

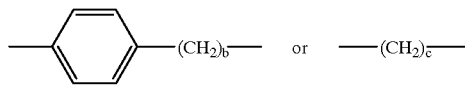

(wherein b is an integer of 0–1 and c is an integer of 1–5)) [preferably, a group of the formula:

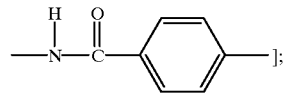

];

Y is a group of the formula: —CO—$R^7$ (wherein $R^7$ is (1) a hydroxy group, (2) a $C_{1-8}$ alkoxy group or a $C_{2-12}$ alkenyloxy group, each of which may be substituted with a substituent selected from a $C_{1-4}$ alkoxy-carbonyl group or a 5-methyl-2-oxo-1,3-dioxolen-4-yl group, or (3) a group of the formula: —OCH($R^{7a}$)OCOR$^8$ (wherein $R^{7a}$ is a hydrogen atom or a $C_{1-6}$ alkyl group and $R^8$ is a $C_{1-6}$ alkyl group or a $C_{5-7}$ cycloalkyloxy group)) [preferably, a carboxyl group]; and n is an integer of 1–4 [preferably, an integer of 2–3]; is preferable.

More preferred examples of the 2-piperazinone-1-acetic acid derivative (I) include (S)-4-(4-guanidinobenzoylamino) acetyl-3-[3-(4-guanidinobenzoylamino)]propyl-2-oxopiperazine-1-acetic acid, (S)-4-(4-amidinobenzoylamino)acetyl-3-[3-(4-amidinobenzoylamino)] propyl-2-oxopiperazine-1-acetic acid, or their hydrochloride, dihydrochloride, acetate, etc. Among others, hydrochloride of (S)-4-(4-guanidinobenzoylamino)acetyl-3-[3-(4-guanidinobenzoylamino)]propyl-2-oxopiperazine-1-acetic acid is preferable and, in particular, (S)-4-(4-guanidinobenzoylamino)acetyl-3-[3-(4-guanidino-benzoylamino)]propyl-2-oxopiperazine-1-acetic acid hydrochloride or (S)-4-(4-guanidinobenzoylamino)acetyl-3-[3-(4-guanidinobenzoylamino)]propyl-2-oxopiperazine-1-acetic acid dihydrochloride is preferable. Said (S)-4-(4-guanidinobenzoylamino)acetyl-3-[3-(4-guanidino-benzoylamino)]propyl-2-oxopiperazine-1-acetic acid dihydrochloride can be prepared by adding concentrated hydrochloric acid to a solution containing (S)-4-(4-guanidinobenzoylamino)acetyl-3-[3-(4-guanidino-benzoylamino)]propyl-2-oxopiperazine-1-acetic acid hydrochloride and adjusting pH of the solution to about 1–2 (preferably about 1.5), and the obtained (S)-4-(4-guanidinobenzoylamino)acetyl-3-[3-(4-guanidino-benzoylamino)]propyl-2-oxopiperazine-1-acetic acid dihydrochloride can be crystallized with ethanol, etc.

Examples of the above-mentioned anti-tumor agents include bleomycin, methotrexate, actinomycin D, mitomycin C, vinblastine sulfate, vincristine sulfate, daunorbicin, adriamycin, neocarzinostatin, cytosine arabinoside, fluorouracil, tetrahydrofuryl-5-fluorouracil, krestin, picibanil, lentinan, levamisole, bestatin, glycyrrhizin, polynucleic acids such as poly IC, poly AU, poly ICLC, etc. [Immune Response (Yuichi YAMAMURA and Seiji MORISAWA; 1977), page 143], etc.

Examples of the above-mentioned antibiotics include gentamycin, dibekacin, kanendomycin, lividomycin, tobramycin, amikacin, fradiomycin, sisomycin, tetracycline hydrochloride, oxytetracycline hydrochloride, rolitetracycline, doxycycline hydrochloride, ampicillin, piperacillin, ticarcillin, cefalotin, cefaloridine, cefotiam, cefsulodin, cefmenoxime, cefmetazole, cefazolin, cefotaxime, cefoperazone, ceftizoxime, moxolactam, thienamycin, sulfazecin, azusleonam, etc.

Examples of the above-mentioned antipyretics, analgesics and anti-inflammatory agents include salicylic acid, sulpyrine, flufenamic acid, diclofenac, indomethecin, morphine, pethidine hydrochloride, levorphanol tartarate, oxymorphone, etc.

Examples of the above-mentioned antitussive expectorants include ephedrine hydrochloride, methylephedrine hydrochloride, noscapine hydrochloride, codeine phosphate, dihydrocodeine phosphate, alloclamide hydrochloride, chlorphezianol hydrochloride, picoperidamine hydrochloride, cloperastine, protokylol hydrochloride, isoproterenol hydrochloride, salbutamol sulfate, terebutaline sulfate, etc.

Examples of the above-mentioned sedatives include chlorpromazine, prochlorperazine, trifluoperazine, atropine sulfate, methylscopolamine bromide, etc.

Examples of the above-mentioned muscle relaxants include pridinol methanesulfonate, tubocurarine chloride, pancuronium bromide, etc.

Examples of the above-mentioned antiepileptic agents include phenytoin, ethosukimide, acetazolamide sodium, chlordiazepoxide, etc.

Examples of the above-mentioned antiulcer agent include metoclopramide, histidine hydrochloride, etc.

Examples of the above-mentioned antidepressants include imipramine, clomipramine, noxiptilin, phenelzine sulfate, etc.

Examples of the above-mentioned antiallergic agents include diphenhydramine hydrochloride, chlorpheniramine maleate, tripelennamine hydrochloride, clemizole hydrochloride, diphenylpyraline hydrochloride, methoxyphenamine hydrochloride, etc.

Examples of the above-mentioned cardiotonics include transbioxocamphor, theophyllol, aminophylline, etilefrine hydrochloride, etc.

Examples of the above-mentioned antiarrhythmic agents include propranolol, alprenolol, bufetolol, oxyprenolol, etc.

Examples of the above-mentioned vasodilators include oxyfedrine hydrochloride, diltiazem, tolazoline hydrochloride, hexobendine, bamethan sulfate, etc.

Examples of the above-mentioned hypotensive diuretics include hexamethonium bromide, pentolinium, mecamylamine hydrochloride, ecarazine hydrochloride, clonidine, etc.

Examples of the above-mentioned antidiabetic agents include glymidine sodium, glipizide, phenformin hydrochloride, buformin hydrochloride, metformin, etc.

Examples of the above-mentioned anticoagulants include heparin sodium, sodium citrate, etc.

Examples of the above-mentioned hemostatics include thromboplastin, thrombin, menadione sodium bisulfite, acetomenaphthone, ε-aminocaproic acid, tranexamic acid, carbazochrome sodium sulfate, adrenochrome monoaminoguanidine methanesulfonate, etc.

Examples of the above-mentioned antituberculous agents include isoniazid, ethambutol, para-aminosalicylic acid, etc.

Examples of the above-mentioned hormone preparations include prednisolone, prednisolone sodium phosphate, dexamethasone sodium sulfate, betamethasone sodium phosphate, hexoestrol phosphate, hexoestrol acetate, methimazole, etc.

Examples of the above-mentioned narcotic antagonists include levallorphan tartarate, nalorphine hydrochloride, naloxone hydrochloride, etc.

Examples of the above-mentioned bone resorption inhibitors include (sulfur-containing alkyl)aminomethylenebisphosphonic acid, etc.

Examples of the above-mentioned osteogenesis promoting agents include vitamin K2 or parathyroid hormone, or a compound of the formula (II):

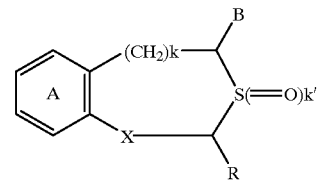

wherein ring A is an optionally substituted benzene ring, R is a hydrogen atom or an optionally substituted hydrocarbon group, B is an optionally esterified or amidated carboxyl group, X is —CH(OH)— or —CO—, k is 0 or 1, and k' is 0, 1 or 2, or a salt thereof, etc. (JP-A H3(1991)-232880, JP-A H4(1992)-364179).

Examples of the above-mentioned angiogenesis inhibitors include angiostatic steroid [Science, 221, 719 (1983)], fumagillin [EP-A-325199], fumagillol derivatives [EP-A-357061, EP-A-359036, EP-A-386667, EP-A-415294], etc.

The physiologically active substance may be distinct entity or in the form of any possible pharmaceutical salts thereof (e.g. a salt with an inorganic acid such as hydrochloric acid, sulfuric acid, nitric acid, etc. or a salt with an organic salt such as carbonic acid, succinic acid, etc., when the physiologically active substance has a basic group such as an amino group, etc.; a salt with an inorganic base such as alkaline metals (e.g. sodium, potassium, etc.), a salt with a basic organic compound such as organic amines (e.g. triethylamine, etc.), basic amino acids (e.g. arginine, etc.), etc., when the physiologically active substance has an acidic group such as carboxyl group, etc.). When the physiologically active substance is distinct entity and water-insoluble, it can be converted into a water-soluble salt thereof.

In the sustained-release microcapsule, the amount of the physiologically active substance to be used varies with factors related to the particular kind of the physiologically active substance, desired pharmacological activity, duration time, etc. The amount of the physiologically active substance in the microcapsule ranges preferably from about 0.01% to about 50% (W/W), more preferably from about 0.1% to about 30% (W/W).

Examples of the biodegradable polymer to be used in the present invention include poly fatty acid esters (e.g. polylactic acid, polyglycolic acid, polycitric acid, polymalic acid, polylactic acid caprolactone, etc.), poly-α-cyanoacrylic acid esters, poly-β-hydroxybutyric acids, polyalkylene oxalates (e.g. polytrimethyleneoxalate, polytetramethyleneoxalate, etc.), polyortho-esters, polyortho-carbonates, other polycarbonates (e.g. polyethylene-carbonate, polyethylene-propylene-carbonate, etc.), polyamino acids (e.g. poly-γ-benzyl-L-glutamic acid, poly-L-alanine, poly-γ-methyl-L-glutamic acid, etc.), hyaluronic acid esters, etc.

These polymers may optionally be used singly or as a copolymer of two or more of them or as a simple mixture of them or in the form of their salts.

The biodegradablity of these biodegradable polymer is defined as the percentage (w/w %) of water-soluble low-molecular weight fragments degraded from the polymer relative to the polymer when the polymer is used as injectable preparations, and in general, it should be not less than 10% in three months after subcutaneous or intramuscular administration, preferably, not less than 80% in one year after subcutaneous or intramuscular administration.

Said biodegradable polymer is preferably aliphatic polyester. Examples of said biodegradable polymer include an aliphatic polyester (a poly fatty acid ester), more preferably, polymers or copolymers of hydroxycarboxylic, or mixtures thereof.

The hydroxycarboxylic acids are not specifically limited, but preferably hydroxycarboxylic acids of the formula:

wherein R is a hydrogen atom or an alkyl group.

In the above formula, examples of the alkyl group represented by R includes a straight or branched alkyl group having 1 to 8 carbon atoms (e.g. methyl, ethyl, propyl, isopropyl, butyl, isobutyl, tertiary butyl, pentyl, hexyl, heptyl, octyl, etc.). Among others, a straight or branched alkyl group having 1 to 3 carbon atoms is more preferable.

Preferred examples of the above hydroxycarboxylic acid include glycolic acid, lactic acid, hydroxybutyric acid (e.g. 2-hydroxybutyric acid), 2'-hydroxyvaleric acid, 2-hydroxy-3-methylbutyric acid, 2-hydroxycaproic acid, 2-hydroxyisocaproic acid, 2-hydroxycaprylic acid, etc. Among others, glycolic acid, lactic acid, 2-hydroxybutyric acid, 2-hydroxy-3-methylbutyric acid, 2-hydroxycaproic acid, etc. are preferable. In particular, glycolic acid, lactic acid, 2-hydroxybutyric acid, etc. are more preferable. Where these hydroxycarboxylic acids exist as D-isomers, L-isomers and D, L-isomers (racemic mixtures of D-isomer and L-isomer), any one of them may be used. Preferably, D,L-isomers are used.

The copolymers may be any of random, block and graft copolymers. Preferred examples of the glycolic acid copolymer include the copolymer that degrades in living body relatively rapidly and has a release period of not more than one month when used alone. In particular, lactic acid/glycolic acid homopolymer or copolymer (hereinafter, referred to as "lactic acid/glycolic acid polymer" or abbreviated to "PLGA", both of which always include copolymers and homopolymers of the respective acids) or hydroxybutyric acid/glycolic acid homopolymer or copolymer (hereinafter, referred to as "hydroxybutyric acid/glycolic acid copolymer", which always include copolymers and homopolymers of the respective acids) is preferable.

The biodegradable polymer to be used in the present invention can be synthesized by general synthetic methods (e.g. those described in JP-A S61(1986)-28521), without any problem.

In general, the weight-average molecular weight of the biodegradable polymer to be used in the present invention ranges preferably from about 2,000 to about 800,000, more preferably from about 5,000 to about 200,000. When lactic acid/glycolic acid copolymer is used as the above-mentioned polymer, the molar ratio of lactic acid/glycolic acid ranges preferably from 100/0 to about 25/75, more preferably from about 100/0 to about 50/50. The weight-average molecular weight of lactic acid/glycolic acid copolymer ranges preferably about 5,000 to about 30,000, more preferably from about 5,000 to about 20,000.

When hydroxybutyric acid/glycolic acid copolymer (e.g. 2-hydroxybutyric acid/glycolic acid copolymer) is used as the above-mentioned polymer, the molar ratio of hydroxybutyric acid/glycolic acid ranges preferably from about 100/0 to about 25/75, more preferably from about 100/0 to about 50/50. In particular, the molar ratio of 2-hydroxybutyric acid/glycolic acid ranges from preferably about 60/40 to about 30/70. The weight-average molecular weight of hydroxybutyric acid/glycolic acid copolymer ranges preferably from about 5,000 to about 25,000, more preferably from about 5,000 to about 20,000.

When butyric acid/glycolic acid copolymer is used as the above-mentioned polymer, the molar ratio of butyric acid/glycolic acid ranges preferably from about 100/0 to about 25/75.

When a mixture of polylactic acid (A) and glycolic acid/2-hydroxybutyric acid copolymer(B) is used as the above-mentioned polymer, the mixing ratio of (A)/(B) ranges from about 10/90 to about 90/10 (by weight), preferably from about 25/75 to about 75/25 (by weight). The weight-average molecular weight of polylactic acid ranges preferably from about 5,000 to about 30,000, more preferably from about 6,000 to about 20,000.

In the present specification, the weight-average molecular weight means a molecular weight in terms of the molecular weight of polystyrene determined by gel permeation chromatography (GPC) using polystyrene as the standard material. More specifically, the weight-average molecular weight is based on polystyrene, obtained by gel permeation chromatography (GPC) with 9 polymers of polystyrene as reference substances with weight-average molecular weights of 120,000, 52,000, 22,000, 9,200, 5,050, 2,950, 1,055, 580 and 162, respectively. The determination was carried out using GPC column KF804L$^x$2 (manufactured by Showa Denko K.K., Japan) and RI monitor L-3300 (Hitachi, Japan) and using chloroform as the mobile phase.

The polydispersity of said polymer is defined as the value of weight average molecular weight/number average molecular weight, which ranges, in general, from 1 to 3.5, preferably from 1.5 to 2.5. The amount of the biodegradable polymer to be used depends upon, for example, the degree of the pharmacological activity of the physiologically active substance, release rate of said substance, release period of said substance, etc. For example, the polymer is used is used as the microcapsule base in an amount of about 0.2 to about 10000 times (by weight), preferably about 1 to about 1000 times (by weight) relative to the weight of the physiologically active substance. The concentration of the biodegradable polymer in an oil phase ranges preferably from about 0.5 to about 90% (W/W), more preferably about 2 to about 60% (W/W).

Examples of the "fat and oil" to be added to an organic solvent of the above biodegradable polymer include any fat and oil which is dissolved in said organic solvent without causing phase separation and which is degradable and absorbable in living body, and preferably excluding a fatty acid, a salt thereof, a glycerin fatty acid ester and a propylene glycol fatty acid ester. Examples of the fat and oil include an oil soluble vitamin (vitamin A, vitamin D, vitamin E, vitamin K, etc.), medium chain fatty acid triglyceride (triglycerol of fatty acid having 8–12 carbon atoms such as miglyol, etc.), cholesterol, phospholipids, etc. Preferable examples of the fat and oil include an oil soluble vitamin (vitamin A, vitamin D, vitamin E, vitamin K, etc.), cholesterol, phospholipids, etc., more preferably an oil soluble vitamin such as α-tocopherol (vitamin E), α-tocopherol acetate (vitamin E acetate), etc.

A final concentration of the fat and oil to be added to an organic solvent of the above biodegradable polymer ranges from about 1% to about 50% (W/W), more preferably from about 3% to about 30% (W/W) relative to a whole content of the sustained-release microcapsules.

In the present invention, when the sustained-release microcapsules are produced by a W/O technique or a W/O/W technique, a basic substance may be further added to an aqueous phase containing the physiologically active substance. In particular, when the physiologically active substance is an acidic drug or an acidic salt of the drug (hydrochloride, etc.) (for example, pH of the aqueous phase is 6 or less), it is preferable to add the basic substance. Examples of the basic substance include a basic amino acid such as L-histidine, L-arginine, L-lysine, etc., N-methylglucamine, etc.

The final concentration of the basic substance to be added to the solution of the physiologically active substance ranges from about 0.1% to about 20% (W/W) relative to a whole content of the sustained-release microcapsule, more preferably about 1% to about 8% (W/W). In the present invention, it is preferable to allow an osmotic pressure adjustor to be contained in the outer aqueous phase when removal of the organic solvent is carried out by in-water drying.

Any osmotic pressure adjustor can be employed so long as it produces osmotic pressure in an aqueous solution thereof.

Examples of the osmotic pressure adjustor include water-soluble polyhydric alcohols, water-soluble monovalent alcohols, water-soluble inorganic materials (e.g. inorganic salts), water-soluble monosaccharides, disaccharides, oligosaccharides polysaccharides or its derivative, water-soluble organic acids or a salt thereof, water-soluble amino acid, water-soluble peptide, protein or its derivative, etc. Among others, water-soluble polyhydric alcohols, water-soluble inorganic materials, water-soluble monosaccharides, disaccharides, oligosaccharides polysaccharides or its derivative, water-soluble organic acid or a salt thereof, etc. are preferable. In particular, salts, water-soluble polyhydric alcohols and water-soluble inorganic materials are preferable.

Examples of the above water-soluble inorganic salts include halogenated alkali metals such as potassium chloride, sodium chloride, potassium bromide, sodium bromide, potassium iodide, sodium iodide, etc., halogenated alkaline earth metals such as calcium chloride, magnesium chloride, etc., alkali metal sulfates such as sodium sulfate, potassium sulfate, etc., alkaline earth metal sulfates such as magnesium sulfate, calcium sulfate, etc., alkali metal phosphates such as potassium dihydrogenphosphate, dipotassium hydrogenphosphate, potassium phosphate, sodium dihydrogenphosphate, disodium hydrogenphosphate, sodium phosphate, etc., etc. Among others, sodium chloride is preferable.

Examples of the above water-soluble polyhydric alcohol include dihyrdic alcohols such as glycerin, etc., pentahydric alcohols such as arabitol, xylitol, adonitol, etc., hexahydric alcohols such as mannitol, sorbitol, etc., etc. Among others, hexahydric alcohols are preferable. Examples of the above water-soluble monovalent alcohol include methanol, ethanol, isopropyl alcohol, etc. Among others, ethanol is preferable. Examples of the above water-soluble monosaccharides include pentoses such as arabinose, xylose, ribose, 2-deoxyribose, etc., hexoses suchas glucose, fructose, galactose, mannose, sorbose, rhamnose, fucose, etc. Among others, hexoses are preferable.

Examples of the above water-soluble disaccharides include maltose, cellobiose, α-trehalose, lactose, sucrose, etc. Among others, lactose and sucrose are preferable.

Examples of the above water-soluble oligosaccharides include trisaccharides such as maltotriose, raffinose, etc., tetrasaccharides such as stachyose, etc., etc. Among others, trisaccharides are preferable.

Examples of the above water-soluble polysaccharides include glucans such as cellulose, starch, glycogen, etc., galacturonans such as pectic acid, etc., mannuronans such as alginic acid, etc., fructans such as inulin, levan, etc., N-acetylglycosamine polymers, such as chitin, etc., xylans such as xylan of rice straw, etc., diheteroglucans such as mannan, glucomannan, galactomannan, hyaluronic acid, chondroitin sulfate, heparin, etc., etc. Among others, glucans, diheteroglucans, etc. are preferable.

Examples of the derivatives of the above water-soluble monosaccharides, disaccharides, oligosaccharides and polysaccharides include glucosamine, galactosamine, glucuronic acid, galacturonic acid, etc. Examples of the above water-soluble organic acid or a salt thereof include citric acid, tartaric acid, malic acid, their alkali metal salt (e.g. sodium salt, potassium salt, etc.), etc. Examples of the above water-soluble amino acid include neutral amino acid such as glycine, alanine, valine, leucine, isoleucine, phenylalanine, tyrosine, tryptophan, serine, threonine, proline, hydroxyproline, cyctein, methionine, etc., acidic amino acid such as aspartic acid, glutamic acid, etc., basic amino acid such as lysine, arginine, histidine, etc., etc. Salts of these water-soluble amino acid with acids (e.g. hydrochloric acid, sulfuric acid, phosphoric acid, etc.) or alkalis (e.g. alkali metal such as sodium, potassium, etc., etc.) are also used optionally. Examples of the water-soluble peptide, protein or their derivative include casein, globulin, prolamin, albumin, gelatin, protamine, histone, etc.

These osmotic pressure adjustor may be used alone or as a mixture of two or more of them. When the osmotic pressure adjustor is a non-ionic material, the concentration of the osmotic pressure adjustor in the outer aqueous phase ranges from about 0.001 to about 60% (W/W), preferably from about 0.01 to about 40% (W/W), more preferably from about 0.05 to about 30% (W/W). When the osmotic pressure adjustor is an ionic material, it is used in a concentration calculated by dividing the above-mentioned concentration by the total ionic valency. The concentration of the osmotic pressure adjustor to be added is not necessarily below their solubility, and a part of it may be left in the state of dispersion in the solvent.

Each step of the production method of the present invention is carried out, for example, as follows:

In the process for producing the microcapsule where a solution of the water-soluble physiologically active substance is used as an aqueous phase, the water-soluble physiologically active substance (hereinafter,briefly referred to as the drug) is dissolved in water, and if necessary, basic substances such as above-mentioned basic amino acid, etc. and additionally pharmaceutical carriers such as e.g. gelatin, agar, polyvinyl-alcohol, etc. are added to the solution to prepare an aqueous phase (an inner aqueous phase).

The concentration of the drug in the inner aqueous phase ranges preferably from about 0.1 to about 150% (W/V), more preferably about 20 to about 130% (W/V), and in particular, about 60 to about 120% (W/V).

As pH regulators to maintain the stability and solubility of the drug, for example, carbonic acid, acetic acid, oxalic acid, citric acid, phosphoric acid, hydrochloric acid, sodium hydroxide, arginine, lysine and their salts, etc. can be added to said aqueous phase. Further, as stabilizers of the drug, there can be added, for example, albumin, gelatin, citric acid, sodium ethylenediaminetetraacetate, dextrin, sodium hydrogensulfite, polyols such as polyethyleneglycol, etc., etc., and as preservatives there can be added, for example, conventional para-oxybenzoic acid esters (e.g. methylparaben, propylparaben, etc.), benzylalcohol, chlorobutanol, thimerosal, etc.

The thus obtained aqueous phase is added to a uniform organic solvent solution (an oil phase) containing the biodegradable polymer (hereinafter, briefly referred to as the polymer) and a fat and oil, followed by emulsification to prepare a W/O type emulsion. The emulsification can be carried out by conventional dispersion techniques such as intermittent shaking, mixing by means of a mixer (e.g. propeller agitator, turbine agitator, etc.), colloid mill operation, mechanical homogenization, ultrasonication, etc.

The above polymer solution (oil phase) can be prepared by dissolving the polymer in an organic solvent which does not substantially mix with water. The water-solubility of said organic solvent is preferably not more than 3% (W/W) at standard temperature (20° C.), and the boiling point of said organic solvent is preferably not more than 120° C. Examples of the organic solvent include halogenated hydrocarbons (e.g. dichloromethane, chloroform, chloroethane, trichloroethane, carbon tetrachloride, etc.), alkyl ethers having 3 or more carbon atoms (e.g. isopropylether, etc.), fatty acid alkyl (having 4 or more carbon atoms) esters (e.g. butyl acetate, etc.), aromatic hydrocarbons (e.g. benzene, toluene, xylene, etc.), etc. These solvents can be used alone or in combination thereof. As the organic solvent, halogenated hydrocarbons (e.g. dichloromethane, chloroform, chloroethane, trichloroethane, carbon tetrachloride, etc.) are more preferable, and in particular, dichloromethane is preferable.

Removal of the organic solvent from the thus produced W/O type emulsion can be carried out by a conventional method. Examples of the removal method of the organic solvent include spray drying, in-water drying, etc., preferably in-water drying.

In the spray drying technique, the produced W/O type emulsion is ejected in a mist form through a nozzle, etc. into the drying chamber of a spray drier to evaporate the solvent from the finely-divided liquid droplets in a brief time. Examples of the nozzle include a two-fluid nozzle, pressure nozzle, rotary disk nozzle, etc.

In the in-water drying, the produced W/O type emulsion is added to an aqueous phase (an outer aqueous phase) to form a W/O/W type emulsion, followed by removing the organic solvent in the oil phase. The volume of the outer aqueous phase is generally selected from the range of about 1 to about 10,000 times the volume of the oil phase, more preferably about 2 to about 5,000 times, and in particular, about 5 to about 2,000 times.

Any emulsifier may be added to the above outer aqueous phase, as long as it can contribute to the formation of a stable W/O/W type emulsion. Examples of the emulsifiers include anionic surfactants (sodium oleate, sodium stearate, sodium lauryl sulfate, etc.), non-ionic surfactants (polyoxyethylene-sorbitan fatty acid esters [Tween 80, Tween 60; Atlas Powder], polyoxyethylene-castor oil derivatives [HCO-60, HCO-50; Nikko Chemicals], etc.), polyvinylpyrrolidone, polyvinylalcohol, carboxymethylcellulose, lecithin, gelatin, hyaluronic acid, etc., preferably polyvinylalcohol. These emulsifiers can be used independently or in combination. The concentration may be selected from about 0.001 to about 20% (W/W), more preferably about 0.01 to about 10% (W/W), and in particular, from about 0.05 to about 5% (W/W).

The above-mentioned osmotic pressure adjustor may be added to an outer aqueous phase. In the production method of the present invention, it is preferable to adjust viscosity of the W/O type emulsion in the range of from about 150 centipoise (cp) to about 10,000 cp when the W/O/W type emulsion is formed.

Examples of the methods to adjust viscosity include (1) a method for adjusting the concentration of the biodegradable polymer in oil phase, (2) a method for adjusting ratio between an amount of the aqueous phase and that of the oil phase, (3) a method for adjusting the temperature of the W/O type emulsion, (4) a method for adjusting the temperature of the outer aqueous, (5) a method for adjusting the temperature of the W/O type emulsion with line heater, cooler, etc. when the W/O type emulsion is injected. Each of these methods may be employed alone or in combination with each other.

Any of the above methods may be employed, as long as viscosity of the W/O type emulsion is in the range of from about 150 cp to about 10,000 cp when the W/O type emulsion is changed into the W/O/W type emulsion.

In the above method (1), the concentration of the biodegradable polymer in oil phase to be adjusted varies depending on the kind of the biodegradable polymer, the kind of the organic solvent, etc., can not be defined as restricted one, and ranges preferably from about 10 to about 80% (W/W).

In the above method (2), ratio between an amount of the aqueous phase and that of the oil phase to be adjusted varies depending on the kind and amount of the drug, the character of the oil phase, etc., can not be defined as restricted one, and ranges preferably W/O=about 1% to about 50% (V/V).

In the above method (3), the temperature of the W/O type emulsion to be adjusted ranges, for example, from about −20° C. to the boiling point of the organic solvent, preferably form about 0° C. to about 30° C., more preferably from about 10° C. to about 20° C.

Adjusting viscosity of the W/O type emulsion in the above methods (1) and (2) can be carried out when the W/O type emulsion is produced.

In the above method (4), before adding the W/O type emulsion to the outer aqueous phase, the temperature of the outer aqueous phase can be adjusted to obtain a similar result in the above method (3). The temperature of the outer aqueous phase ranges, for example, from about 5° C. to about 30° C., preferably from about 10° C. to about 25° C., more preferably from about 12° C. to about 20° C.

The removal of the organic solvent can be carried out by conventional methods. For example, it is carried out by evaporating the organic solvent by stirring with a propeller-type stirrer, magnetic stirrer, etc. under atmospheric pressure or gradually reducing pressure or while controlling degree of vacuum by using a rotary evaporator, etc., etc.

When a water insoluble metal salt (or a metal salt which is hardly soluble in water) of the physiologically active peptide is used as a physiologically active substance, a dispersion which is obtained by dispersing the physiologically active peptide metal salt in the organic solvent containing the biodegradable polymer and the fat and oil is mixed well to give an organic solvent dispersion (hereinafter, referred to as a S/O type emulsion for the sake of convenience) whose stability of dispersion is high and where the physiologically active peptide metal salt is substantially uniformly dispersed or suspended in the organic solvent.

Examples of the above organic solvents include a similar organic solvent to the organic solvent which is used for the preparation of the oil phase containing the biodegradable polymer and the fat and oil in the preparation of the above W/O type emulsion.

For the preparation of the above S/O type emulsion, conventional dispersion techniques can be employed. Examples of the dispersion techniques include intermittent shaking, mixing by means of a mixer (e.g. propeller agitator, turbine agitator, etc.), colloid mill operation, mechanical homogenization, ultrasonication, etc.

In this case, it is useful to use a water-soluble solvent together with a water-insoluble solvent, if desired. As said water-soluble solvent, any solvent can be employed as long as it is water-soluble and can mix with the above water-insoluble solvent. Examples of said water-soluble solvent include alcohols (e.g. methanol, ethanol, propyl alcohol, isopropyl alcohol, etc.), acetone, acetonitrile, etc.

In the preparation of the s/o type emulsion, the physiologically active substance is preferably finely pulverized to microparticles and dispersed in oil phase. The pulverized particle size ranges usually from about 1 nm to about 30 $\mu$m, preferably about 1 nm to about 5 $\mu$m, more preferably about 1 nm to about 1 $\mu$m.

Subsequently, the S/O type emulsion is subjected to removal of the organic solvent according to a similar method applied for the above W/O type emulsion, and in-water drying is preferably employed. Preferably, an osmotic pressure adjustor is allowed to be contained in the outer aqueous phase in the above-mentioned concentration. More specifically, said oil phase is added to the second aqueous phase containing the osmotic pressure adjustor to form an S/O/W type emulsion, followed by removing the organic solvent in the oil phase to prepare microcapsules.

To the outer aqueous phase in the S/O/W type in-water drying method, emulsifiers may be added. Examples of the emulsifiers include a similar emulsifier to those described for the preparation of the above W/O/W type emulsion.

The removal of the organic solvent in the oil phase can be carried out by conventional methods. For example, it is carried out by evaporating the organic solvent by stirring with a propeller-type stirrer, magnetic stirrer, etc. under atmospheric pressure or gradually reducing pressure or while controlling degree of vacuum by using a rotary evaporator, etc., etc. In this case, at the time when solidification of the polymer proceeds in some degree and the loss caused by the release of the physiologically active substance from the internal phase is decreased, the S/O/W type emulsion may be warmed gradually to remove the organic solvent more completely, which results in saving of the required time. Alternatively, when thickening and solidification are carried out by methods other than those based on temperature, the removal can be carried out by merely allowing the S/O/W type emulsion to stand with stirring, by warming it, by spraying nitrogen gas, etc., etc.

This removal step of the organic solvent is of importance and greatly influences the surface structure of microcapsule controlling the release of the physiologically active substance. For example, rapid removal produces a number of pores on the surface or makes pores larger in their size, which results in increased release rate of the physiologically active substance.

The thus obtained microcapsules are collected by centrifugation or filtration. Then, free physiologically active substance, carriers therefor, etc. attached onto the surface of the microcapsules are washed with distilled water repeatedly several times, and water and the solvent in the microcapsules are removed more completely in reduced pressure, if necessary, with warming.

The thus obtained microcapsules are usually dispersed in distilled water, etc., subjected to freeze-drying and stored. In freeze drying, aggregation inhibitors may be added. Examples of said aggregation inhibitors include water-soluble polysaccharides (e.g. mannitol, etc.), starch (e.g. corn starch, etc.), inorganic salts, amino acids, proteins, etc. Among others, mannitol is preferable. Mixing ratio (by weight) between the microcapsules and the aggregation inhibitors ranges about 50:1 to about 1:1, preferably about 20:1 to about 1:1, more preferably about 10:1 to about 5:1. In order to prevent the particles from aggregating with each other while washing, aggregation inhibitors may be added to distilled water as washing solution. Examples of said aggregation inhibitors include water-soluble polysaccharides such as mannitol, lactose, glucose, etc., amino acids such as glycine, etc., proteins such as fibrin, collagen, etc., inorganic salts such as sodium chloride, sodium hydrogen phosphate, etc., etc., preferably mannitol.

After freeze drying, removal of water and an organic solvent may be carried out by warming the microcapsules under reduced pressure, if desired. When warming temperature is less than glass transition temperature of the biodegradable polymer used as a base, improvement of initial release of an excess amount of the physiologically active peptide is not expected. When warming temperature is too high, there increases a danger of melting the microcapsules and attaching to each other, deformation of the microcapsules, decomposition of the physiologically active substance, decrease of activity of the physiologically active substance, etc. In general, warming temperature is selected appropriately, considering properties of the biodegradable polymer used as a base (e.g. molecular weight, stability, etc.), kind of the physiologically active peptide, average particle size of the microcapsules, warming time, degree of dryness of the microcapsules, warming method, etc. Preferably, the microcapsules are warmed and dried at an appropriate temperature which is not less than glass transition temperature of the biodegradable polymer used as a base and where particles of the microcapsules do not attached to each other. In particular, the microcapsules are warmed and dried at temperatures ranging from glass transition temperature to about 30° C. higher than glass transition temperature of the biodegradable polymer used as a base. In this specification, glass transition temperature is defined by median glass transition temperature which is determined using differential scanning calorimeter at temperature increments of 10 or 20° C. per minute.

Warming and drying time varies depending on warming temperature, an amount of the microcapsules to be treated, etc. In general, about 24 to about 120 hours after temperature of microcapsules themselves reach to the desired temperature are preferable. In particular, about 48 to about 120 hours are preferable.

A method for warming the misrocapsules is not limited to a specific method, and any method can be employed as long as the microcapsule are uniformly warmed.

The microcapsules thus obtained are screened, and if necessary, after light pulverization, too large microcapsules are removed by sieving. Particle size of the microcapsules varies with the desired degree of sustained release. When the microcapsules are used as suspension, particle size of the microcapsules are selected from the range satisfying the dispersibility and needle-pass requirements. For example, the average diameter ranges preferably from about 0.5 to 400 μm, more preferably about 2 to 200 μm.

In order to prepare a sterile preparation of the microcapsules, a method for sterilizing all production steps, a method for sterilizing with γ-rays, a method for adding a preservative, etc. are employed, and there is no limitation to a specific method.

The microcapsules prepared according to the process of the present invention can be readily administered orally or non-orally, for example, as injections or implants intramuscularly, subcutaneously, into blood vessels, organs, cava articulare, foci, etc. Further, they can be administered in the form of various preparations. They can also be used as raw materials in the production of various preparations.

Examples of the above preparation include injections, oral preparations (e.g. powders, granules, capsules, tablets), nasal preparations, suppositories (e.g. rectal suppositories, vaginal suppositories), etc.

These preparations can be produced according to conventional methods. For example, when the microcapsules according to the present invention are to be processed into injections, the microcapsules of the present invention are dispersed in a aqueous vehicle together with a dispersing agent (e.g. Tween 80, HCO 60 (Nikko Chemicals), carboxymethyl-cellulose, sodium arginate, etc.), a preservative (e.g. methylparaben, propylparaben, benzylalcohol, chlorobutanol, etc.), a tonicity agent (e.g. sodium chloride, glycerin, sorbitol, glucose, etc.), etc., or an oily vehicle such as vegetable oils (e.g. olive oil, sesame oil, peanut oil, cotton-seed oil, corn oil, etc., propylene glycol, etc., to prepare sustained-release injections of the microcapsules. Further, excipients (e.g. mannitol, sorbitol, lactose, glucose, etc.) may be added, in addition to the above components, to the above sustained-release injections of the microcapsules in the form of suspensions. After redispersion, the injections are solidified by freeze drying or spray drying, and distilled water for injection or an appropriate dispersing agent may be added just before use. In this manner, more stable sustained-release injections can be obtained.

When the microcapsules according to the present invention are to be processed into, for example, tablets, they can be prepared according to conventional preparation methods. For example, there can be added excipients (e.g. lactose, crystalline cellulose, sucrose, starch such as corn starch, etc., etc.), disintegrating agents (e.g. starch such as corn starch, etc., croscarmellose sodium, carboxymethylstarch sodium, calcium carmonate, etc.), binders (e.g. crystalline cellulose, gum arabic, dextrin, carboxymethylcellulose, polyvinylpyrrolidone, hydroxypropylcellulose, etc.), lubricants (e.g. talc, magnesium stearate, polyethylene glycol 6000, etc.), etc. to the microcapsules, and the mixture is compressed for molding.

When the microcapsules according to the present invention are to be processed into, for example, nasal preparations, they are molded into solid, semisolid or liquid. In any case, conventional preparation methods can be used. For example, to prepare the above solid nasal preparations, said microcapsules either as they are or together with excipients (e.g. glucose, mannitol, starch, microcrystalline cellulose, etc.), thickeners (e.g. natural gums, cellulose derivatives, polyacrylates, etc.), etc. are processed into powdery compositions. To prepare the above liquid nasal preparations, said microcapsules are processed into an oily or aqueous suspension in substantially the same manner as injections. The semisolid nasal preparations may be oily or aqueous gels or ointments. In any case, there may be added a pH adjustor (e.g. carbonic acid, phosphoric acid, citric acid, hydrochloric acid, sodium hydroxide, etc.), a preservative (e.g. paraoxybenzoic acid esters, chlorobutanol, benzalkonium chloride, etc.), etc.

When the microcapsules according to the present invention are to be processed into suppositories, they can be prepared per se known methods in the form of oily or aqueous solid, semisolid or liquid, with using an oily or aqueous base. Examples of the oily base to be used for the above composition include any one which does not dissolve the microcapsules, for example, higher fatty acid glycerides [e.g. cacao butter, Witepsols (Dynamit-Nobel), etc.], medium chain fatty acid triglycerides [e.g. miglyols (Dynamit-Nobel), etc.], vegetable oils (e.g. sesame oil, soybean oil, cottonseed oil, etc.), etc. Examples of the aqueous base include polyethyleneglycols, propyleneglycols, etc. Examples of the aqueous gels include natural gums, cellulose derivatives, vinyl polymers, polyacrylates, etc.

The microcapsules obtained according to the production method of the present invention suppress initial burst and release a constant amount of the drug for a long time. Therefore, the microcapsules obtained according to the production method of the present invention exhibits a constant efficacy with low toxicity, thus being expected as a safe and highly effective sustained-release preparation. In addition, when the microcapsules are applied for the treatment of chronic disease, physical burden can be lightened and compliance can be improved in a patient who has to receive frequent administrations.

For example, in case of pituitary dwarfism, administration of growth hormone is inevitable and so far growth hormone is subcutaneously or intramuscularly administered to infants or juvenile patients every day or every second day for several months to 10 years ormore. Sincethe sustained-release microcapsule obtained by the production method of the present invention provide these patients with sufficient treatment effect with one administration within several weeks to months, it can contribute to improvement of compliance in these patients.

For example, when the sustained-release microcapsule of the present invention containing a water-soluble physiologically active substance which is an antithrombus agent is used for the treatment of thrombosis, the sustained-release microcapsule of the present invention can stably maintain blood level of the drug within an effective dose which does not cause any side effect for a long time, while there is fear that a conventional method for administering an antithrombus agent causes bleeding as side effect of antithrombus activity. Therefore, the sustained-release microcapsule of the present invention can be positively used not only for the treatment of said chronic disease for a long time but also for the prevention of the same. Thus, the microcapsule of the present invention shows less side effect and low toxicity, and therefore, can be safely administered to warm blooded mammal such as mouse, rat, dog, horse, bovine, human, etc.

While the dosage of the sustained-release microcapsule varies with the types and content of the physiologically active substance as the principal ingredient, dosage forms, duration of the release of the drug, subject animals, purposes of administration, etc., it is sufficient if only the principal ingredient is contained in an effective amount.

For example, when the sustained-release microcapsule of the physiologically active peptide or a salt thereof is 1-week type sustained-release preparation, the unit dosage for an adult is selected from the range preferably from about 0.0001 to 10 mg/kg, more preferably about 0.0005 to 1 mg/kg.

Number of administrations can be appropriately selected from once a week, once per two weeks, once a month, etc., depending on the types and content of the physiologically active substance, dosage forms, duration of the release of the drug, subject diseases, subject animals, etc.

When the physiologically active polypeptide as active ingredient of the.sustained-release preparation is human growth hormone and 2-week type preparation of the sustained-release preparation is administered to a patient of pituitary dwarfism, the unit dosage of the active ingredient is usually selected from about 0.01 to about 5 mg/kg, preferably about 0.03 to about 1 mg/kg, and sustained-release preparation is administered once per two weeks. When the physiologically active substance is insulin, the unit dosage of the active ingredient to a patient of diabetes is usually selected from about 0.001 to about 1 mg/kg, preferably about 0.01 to about 0.2 mg/kg, and sustained-release preparation is administered once a week.

When the sustained-release microcapsule containing 2-piperazinone-1-acetic acid derivative or a salt thereof represented by the above formula (I) which is anticoagulant is orally administered to a patient of unstable angina, or a patient of ischemic complication or reobstruction of coronary or restenosis of coronary after PTCA or coronary thrombolytic therapy, the unit dosage for an adult (body weight: 50 kg) is selected from about 1 mg to 10 g, preferably about 1 mg to 2 g as an amount of the microcapsule (usually, about 1 to 500 mg, preferably about 10 to 200 mg as an amount of Compound (I) as the principal ingredient).

When the sustained-release microcapsule containing 2-piperazinone-1-acetic acid derivative or a salt thereof represented by the above formula (I) is non-orally administered to a patient of unstable angina, or a patient of ischemic complication or reobstruction of coronary or restenosis of coronary after PTCA or coronary thrombolytic therapy, the unit dosage for an adult (body weight: 50 kg) is selected from about 0.1 to 5 ml, preferably about 0.5 to 3 ml as a volume of a suspension to be administered as injection (usually, about 0.05 to 50 mg, preferably 1 to 20 mg as an amount of Compound (I) as the principal ingredient).

The sustained-release microcapsule obtained by the production method of the present invention is stored at standard temperatures or at a cold place, preferably at a cold place. In this specification, standard temperature or a cold place is the same as that defined in The Pharmacopoeia of Japan. That is, standard temperature is 15–25° C., and a cold place is the place where the temperature is 15° C. or less.

EXAMPLES

The present invention is hereinafter described in more detail by means of, but not limited to, the following Working Examples and Test Examples.

Working Example 1

In distilled water 1 ml were dissolved (S)-4-(4-guanidinobenzoylamino)acetyl-3-[3-(4-guanidinobenzoylamino)]propyl-2-oxopiperazine-1-acetic acid (hereinafter, briefly referred to as Compound A) hydrochloride 500 mg and L-arginine 150 mg to give an inner aqueous phase. In methylene chloride 7.5 ml were dissolved lactic acid/glycolic acid copolymer (lactic acid/glycolic acid=50/50 (mole %), weight-average molecular weight 8,000) 3850 mg and vitamin E 500 mg to give an oil phase. The oil phase was added to the inner aqueous phase, and the mixture was emulsified with small homogenizer (Polytron) to give a W/O type emulsion. The W/O emulsion was emulsified in 0.1% PVA solution 800 ml (an outer aqueous phase) containing 2.7% NaCl which was cooled to 15° C. with using homomixer to give a W/O/W type emulsion. Then, the W/O/W type emulsion was slowly stirred with a conventional propeller agitator for 3 hours. After hardening of the microcapsules with evaporation of methylene chloride, the microcapsules were collected by centrifugation. The collected microcapsule were washed with purified water and subjected to freeze drying. The microcapsule 20 mg was dissolved in acetonitrile/distilled water (2:1 mixture) 3 ml. To the mixture was added 0.5 N KOH-ethanol solution 3 ml, and the mixture was subjected to hydrolysis at 25° C. for 20 hours, followed by evaporation under nitrogen gas stream. The residue was neutralized with 0.5 N HCl, and the solution was diluted with 0.01 N HCl to give a solution of a final amino acid concentration at about 200 nmol/ml and subjected to amino acid analyzer (Hitachi L-8500A) to determine the content of arginine. In the microcapsules, the content of arginine was 1.6%, and the content of vitamin E in the microcapsules determined according to a method described in Working Example 5 shown below was 10%.

Working Example 2

In distilled water 1 ml were dissolved Compound A hydrochloride 500 mg and L-arginine 150 mg to give an inner aqueous phase. In methylene chloride 8 ml were dissolved lactic acid/glycolic acid copolymer (lactic acid/glycolic acid=50/50 (mole %), weight-average molecular weight: 8,000) 4100 mg and vitamin E 250 mg to give an oil phase. The oil phase was added to the inner aqueous phase, and the mixture was emulsified with small homogenizer (Polytron) to give a W/O type emulsion. The W/O emulsion was emulsified in 0.1% PVA solution 800 ml (an outer aqueous phase) containing 2.7% NaCl which was cooled to 15° C. with using homomixer to give a W/O/W type emulsion. Then, the W/O/W type emulsion was slowly stirred with a conventional propeller agitator for 3 hours. After hardening of the microcapsules with evaporation of methylene chloride, the microcapsules were collected by centrifugation. The collected microcapsules were washed with purified water, to which was added mannitol 440 mg, and subjected to freeze drying.

Working Example 3

In distilled water 2 ml were dissolved Compound A hydrochloride 750 mg and L-arginine 150 mg to give an inner aqueous phase. In methylene chloride 10 ml were dissolved lactic acid/glycolic acid copolymer (lactic acid/glycolic acid=50/50 (mole %), weight-average molecular weight: 9,000) 3600 mg and vitamin E 500 mg to give an oil phase. According to a similar method described in Working Example 2 the W/O type emulsion was prepared, and thereafter the W/O/W type emulsion was prepared, and finally freeze dried microcapsules was prepared. In the prepared microcapsules, content of arginine and vitamin E was respectively 1.5% (w/w) and 10% (w/w).

Working Example 4

In distilled water 1 ml were dissolved Compound A hydrochloride 500 mg and L-arginine 150 mg to give an inner aqueous phase. In methylene chloride 8 ml were dissolved lactic acid/glycolic acid copolymer (lactic acid/glycolic acid=50/50 (mole %), weight-average molecular weight: 9,000) 4100 mg and vitamin E 250 mg to give an oil phase. According to a similar method described in Working Example 2 the W/O type emulsion was prepared, and thereafter the W/O/W type emulsion was prepared, and finally freeze dried microcapsules was prepared. In the prepared microcapsules, content of arginine and vitamin E was respectively 1.8% (w/w) and 5.2% (w/w).

Comparative Example 1

In distilled water 0.5 ml was dissolved Compound A 200 mg to give an inner aqueous phase. In methylene chloride 2 ml was dissolved lactic acid/glycolic acid copolymer (lactic acid/glycolic acid=50/50 (mole %), weight-average molecular weight 9,000) 1800 mg to give an oil phase. According to a similar method described in Working Example 3 the W/O type emulsion was prepared, and thereafter the W/O/W type emulsion was prepared, and finally freeze dried microcapsules was prepared.

In Table 1, properties of the microcapsules obtained in Working Example 4 and Comparative Example 1 are shown.

TABLE 1

| Method | Entrapment | Initial Release of 1 day in vitro Release Test |
|---|---|---|
| Working Example 4 | 96% | 10% |
| Comparative Example 1 | 88% | 68% |

As shown in Table 1, entrapment ratio of the drug into the microcapsules was increased and initial release of 1 day with in vitro Release Test was suppressed according to the production method of the microcapsules characterized by adding 3% arginine to an inner aqueous phase and 5% vitamin E to an oil phase with using Compound A hydrochloride.

Test Example 1

The microcapsules (20 mg/kg as the drug content) obtained in the above Working Example 1 and Comparative Example 1 were subcutaneously administered to SD rats (male, 6 weeks) and the plasma level of the drug after administration was determined by ELISA, respectively. The thus obtained results were shown in FIG. 1. In FIG. 1, the curve A shows the plasma level of the drug administered by the microcapsules of Working Example 1 and the curve B shows the plasma level of the drug administered by the microcapsules of Comparative Example 1. The plasma level of the drug 1 hour after administration of the microcapsules of Working Example 1 and Comparative Example 1 were respectively 689 ng/ml and 2926 ng/ml. Therefore, it became possible that increase of the plasma level of the drug was suppressed at an early stage after administration, the time-course changes of the plasma level of the drug was not remarkable and the effective plasma level of the drug was stably maintained for about 2 weeks in the microcapsules prepared by adding 3% arginine to an inner aqueous phase and 10% vitamin E to an oil phase with using Compound A hydrochloride.

Reference Example 1

To a solution (710 mg/355 ml, 5 mM $NH_4HCO_3$, pH 7.8) containing recombinant human growth hormone having methionine at its amino terminal (prepared according to the method described in Reference Example 14 of JP-A S62 (1987)-171699) [hereinafter, briefly referred to as Met-hGH] was gradually added dropwise $Zn(OAc)_2 \cdot 2H_2O$ (71 mg/5 ml $H_2O$) solution 3.5 ml (Met-hGH:Zn=1:7 mole) while stirring. The resulting insoluble Met-hGH/Zn complex was centrifuged at 2,500 rpm for 20 minutes, and the supernatant was removed. The insoluble Met-hGH/Zn complex was redispersed in distilled water 100 ml and subjected to freeze drying.

Working Example 5

In a mixture of methylene chloride 2.0 ml and acetonitrile 0.4 ml were dissolved lactic acid/glycolic acid copolymer (lactic acid/glycolic acid=50/50 (mole %), weight-average molecular weight: 15,000; Wako Pure Chemical) 1275 mg and vitamin E 150 mg to give an oil phase. In the oil phase was dispersed Met-hGH/Zn complex 75 mg obtained in Reference Example 1. The dispersion was subjected to ultrasonication for 5 minutes and then to a small homogenizer (Polytron) at 15,000 rpm for 1 minute to pulverize it to microparticles. The S/O dispersion was added to polyvinylpyrrolidone (PVA) solution 800 ml containing 10% mannitol cooled at 15° C. and emulsified with homomixer to give a S/O/W type emulsion. The S/O/W type emulsion was slowly stirred with a conventional propeller agitator for 3 hours. After methylene chloride was vaporized, the resulting microcapsules were collected by centrifugation, washed with purified water and subjected to freeze drying.

To the obtained microcapsules 20 mg were added ethyl acetate 5 ml and 0.1 M acetic acid buffer solution (PH=4) 1 ml. The mixture was shaken for 10 minutes and centrifuged at 2,500 rpm for 10 minutes. Ultraviolet (UV) absorption (294 nm) of the resulting ethyl acetate layer was measured with an spectrophotometer (Beckman DU 7400) to determine the content of vitamin E in the microcapsules. The content of vitamin E in the microcapsules was 10%.

Working Example 6

In a mixture of methylene chloride 2.0 ml and acetonitrile 0.4 ml were dissolved lactic acid/glycolic acid copolymer (lactic acid/glycolic acid=50/50 (mole %), weight-average molecular weight: 15,000) 1350 mg and vitamin E 300 mg to give an oil phase. In the oil phase was dispersed hGH/Zn complex 75 mg obtained in Reference Example 1. The dispersion was subjected to ultrasonication for 5 minutes and then to a small homogenizer (Polytron) at 15,000 rpm for 1 minute to pulverize it to microparticles. According to a similar method described in Working Example 5 the S/O dispersion was prepared, and thereafter the S/O/W type emulsion was prepared, and finally freeze dried microcapsules was prepared. In the prepared microcapsules, the content of vitamin E was 17% when determined by a method described in Working Example 5.

Comparative Example 2

In a mixture of methylene chloride 2.0 ml and acetonitrile 0.4 ml was dissolved lactic acid/glycolic acid copolymer (lactic acid/glycolic acid=50/50 (mole %), weight-average molecular weight: 15,000) 1425 mg to give an oil phase. In the oil phase was dispersed Met-hGH/Zn complex 75 mg obtained in Reference Example 1. The dispersion was subjected to ultra-sonication for 5 minutes and to a small homogenizer (Polytron) at 15,000 rpm for 1 minute to pulverize it to microparticles. According to a similar method described in Working Example 6 the S/O dispersion was prepared, and thereafter the S/O/W type emulsion was prepared, and finally freeze dried microcapsules was prepared.

Test Example 2

Figure 2:
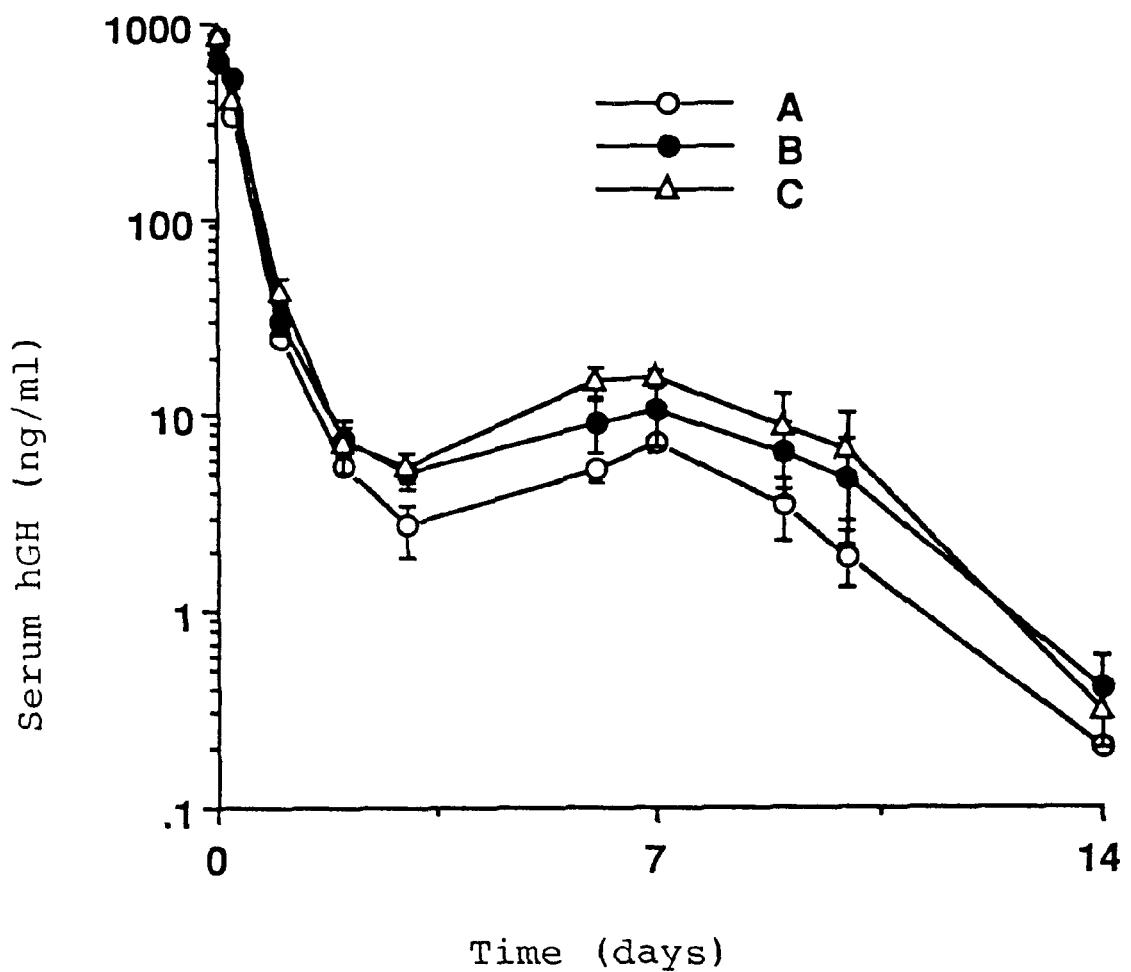
FIG. 2 shows the time-course changes of the plasma level of the drug after administration of the microcapsules used in Test Example 2.

The microcapsules (15 mg/kg as hGH content) obtained in the above Working Example 5. Working Example 6 and Comparative Example 2 were subcutaneously administered to SD rats (male, 6 weeks) and the serum level of hGH was determined by RIA, respectively. The thus obtained results were shown in FIG. 2. In FIG. 2, the curve A shows the serum level of hGH administered by the microcapsules of Comparative Example 2 and the curves B and C show the serum level of the drug administered by the microcapsules of Working Examples 5 and 6, respectively. The plasma level of hGH 1 hour after administration of the microcapsules of Comparative Example 2, Working Example 5 and Working Example 6 were respectively 813 ng/ml, 633 ng/ml and 844 ng/ml. Bioavailabilities (BA) calculated from AUC (area under curve) of drug blood level-time until 2 weeks after administration were respectively 42%, 56% and 57%, compared with intravenous administration of hGH solution. Initial burst (IB) which was calculated by the ratio of AUC until 1 day after administration relative to AUC until 2 weeks after administration were respectively 83%, 79% and 72%.

In the microcapsules containing 10% vitamin E in an oil phase prepared according to Working Example 5, increase of the plasma level (C1 h) of hGH at an early stage (1 hour) after administration was suppressed, the high serum plasma level of hGH was maintained for 2 weeks, and increase of BA and suppress of IB were succeeded.

In the microcapsules containing 17% vitamin E in an oil phase prepared according to Working Example 6, no remarkable change in C1h was observed, the high serum plasma level of hGH was maintained for 2 weeks, and increase of BA and suppress of IB were succeeded.

Working Example 7

In distilled water 1 ml were dissolved Compound A dihydrochloride 500 mg and L-arginine 300 mg to give an inner aqueous phase. In methylene chloride 7.5 ml were dissolved lactic acid/glycolic acid copolymer (lactic acid/glycolic acid=50/50 (mole %), weight-average molecular weight 8,000) 3950 mg and vitamin E 250 mg to give an oil phase. The oil phase was added to the inner aqueous phase, and the mixture was emulsified with small homogenizer (Polytron) to give a W/O type emulsion. The W/O emulsion was emulsified in 0.1% PVA solution 800 ml (an outer aqueous phase) containing 2.7% NaCl which was cooled to 15° C. with using homomixer to give a W/O/W type emulsion. Then, the W/O/W type emulsion was slowly stirred with a conventional propeller agitator for 3 hours. After hardening of the microcapsules with evaporation of methylene chloride, the microcapsules were collected by centrifugation. The collected microcapsule were washed with purified water and subjected to freeze drying. In the microcapsule, entrapment ratio of the drug was 90%.

Working Example 8

In distilled water 1 ml were dissolved Compound A dihydrochloride 500 mg and L-arginine 300 mg to give an inner aqueous phase. In methylene chloride 15 ml were dissolved lactic acid/glycolic acid copolymer (lactic acid/glycolic acid=50/50 (mole %), weight-average molecular weight 10,000) 3160 mg, lactic acid/glycolic acid copolymer (lactic acid/glycolic acid=50/50 (mole %), weight-average molecular weight 7,000) 790 mg and vitamin E 250 mg to give an oil phase. The oil phase was added to the inner aqueous phase, and the mixture was emulsified with small homogenizer (Polytron) to give a W/O type emulsion. The W/O emulsion was emulsified in 0.1% PVA solution 800 ml (an outer aqueous phase) containing 2.7% NaCl which was cooled to 15° C. with using homomixer to give a W/O/W type emulsion. Then, the W/O/W type emulsion was slowly stirred with a conventional propeller agitator for 3 hours. After hardening of the microcapsules with evaporation of methylene chloride, the microcapsules were collected by centrifugation. In the microcapsule, entrapment ratio of the drug was 91%.

EFFECT OF THE INVENTION

According to the present invention, the microcapsules which contains high amount of a physiologically active substance and stable release of the drug with less initial release can be prepared by adding a fat and oil which is dissolved in an organic solvent containing biodegradable polymer without causing phase separation. By using said microcapsules, side effect of the physiologically active substance can be decreased, the physiologically active substance can be administered for a long time, and compliance of patients can be improved due to decrease of the number of administrations.

What is claimed is:

1. A process for producing a sustained-release microcapsule, comprising the steps of:
   (a) selecting a water-soluble physiologically active substance;
   (b) dissolving said water-soluble physiologically active substance in water to form an inner aqueous phase, said inner aqueous phase further comprising a basic substance;
   (c) dissolving a biodegradable polymer and vitamin E in an organic solvent to form an organic solvent phase;
   (d) admixing said aqueous phase and said organic solvent phase to form a water/oil emulsion;
   (e) dispersing the water/oil emulsion in an outer aqueous phase to form a water/oil/water emulsion; and
   (f) removing the organic solvent from said water/oil/water emulsion of step (e) by in-water drying.

2. A process according to claim 1, wherein the water-soluble physiologically active substance is a polypeptide the molecular weight of which ranges from about 200 to about 80,000.

3. A process according to claim 1, wherein the water-soluble physiologically active substance is an integrin antagonist.

4. A process according to claim 3, wherein the integrin antagonist is a GPIIb/IIIa antagonist.

5. A process according to claim 4, wherein the GPIIb/IIIa antagonist is a 2-piperazinone-1-acetic acid derivative represented by the formula (I):

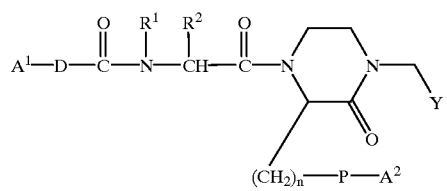

wherein $A^1$ and $A^2$ are independently a proton-accepting group or a group convertible into a proton-accepting group, D is a spacer having a 2- to 6-atomic chain optionally bonded through a hetero atom and/or a 5- or 6-membered ring (provided that the 5- or 6-membered ring is counted as 2- or 3-atomic chain, depending on its bonding position), $R^1$ is a hydrogen atom or hydrocarbon group, $R^2$ is a hydrogen atom or a residual group formed by removing —CH (NH$_2$) COOH from an α-amino acid, or R$^1$ and R$^2$ may be combined to form a 5- or 6-membered ring, P is a spacer having a 1- to 10-atomic chain optionally bonded through a hetero atom and/or a 5- or 6-membered ring (provided that the 5- or 6-membered ring is counted as 2- or 3-atomic chain, depending on its bonding position), Y is an optionally esterified or amidated carboxyl group, and n is an integer of 0–8; or a salt thereof.

6. A process according to claim 5, wherein the 2-piperazinone-1-acetic acid derivative (I) is (S)-4-(4-guanidinobenzoylamino)acetyl-3-[3-(4-guanidinobenzoylamino)]propyl-2-oxopiperazine-1-acetic acid or a salt thereof.

7. A process according to claim 5, wherein the 2-piperazinone-1-acetic acid derivative (I) is (S)-4-(4-guanidinobenzoylamino)acetyl-3-[3-(4-guanidinobenzoylamino)]propyl-2-oxopiperazine-1-acetic acid hydrochloride.

8. A process according to claim 5, wherein the 2-piperazinone-1-acetic acid derivative (I) is (S)-4-(4-guanidinobenzoylamino)acetyl-3-[3-(4-guanidinobenzoylamino)]propyl-2-oxopiperazine-1-acetic acid dihydrochloride.

9. A process according to claim 1, wherein the biodegradable polymer is an aliphatic polyester.

10. A process according to claim 9, wherein the aliphatic polyester is a lactic acid/glycolic acid copolymer.

11. A process according to claim 1, wherein the basic substance in said inner aqueous phase is an amino acid.

12. A process according to claim 11, wherein the basic amino acid is L-arginine.

13. A process according to claim 11 or 12, wherein the final concentration of the basic substance in the sustained release microcapsule is about 1% to about 8% (w/w).

14. A sustained-release microcapsule produced by the process according to claim 1.

* * * * *

UNITED STATES PATENT AND TRADEMARK OFFICE
CERTIFICATE OF CORRECTION

PATENT NO.     : 6,287,587 B2
DATED          : September 11, 2001
INVENTOR(S)    : Takada Shigeyuki et al.

It is certified that error appears in the above-identified patent and that said Letters Patent is hereby corrected as shown below:

Title page,
Item [57], ABSTRACT,
Line 2, "contains" should read -- contain --; and "suppresses" should read -- suppress --; and
Line 3, "shows" should read -- show --.

Column 1,
Line 47, "contains" should read -- contain --; and
Line 55, "contains" should read -- contain --.

Column 2,
Line 10, "releases" should read -- release --;
Line 22, "invention" should read -- inventors --;
Line 32, "said" should read -- a --; and
Line 43, "an" (second occurrence) should read -- a --.

Column 3,
Line 55, "an" (second occurrence) should read -- a --.

Column 4,
Line 5, "an" should read -- a --;
Line 16, "hormone.;" should read -- hormone; --;
Line 31, "peptide;" should read -- peptide, --;
Line 33, "DRAWING" should read -- DRAWINGS --; and
Line 44, "etc." should read -- etc., --; and
Line 51, "etc." should read -- etc., --.

Column 5,
Line 11, "said" should read -- This --;
Line 24, "NGF-1," (second occurrence) should read -- NGF-2, --;
Line 26, "factor(PDGF)," should read -- factor (PDGF), --;
Line 27, "bFGF," should read -- bFGF, etc.), --;
Line 42, "thyroid-stimulatinghormone" should read -- thyroid-stimulating hormone --;
Line 43, "stimulatinghormone" should read -- stimulating hormone --;
Line 47, "include" should read -- may include --;
Line 51, "include" should read -- may include --;
Line 58, "etc." should read -- etc., --.

UNITED STATES PATENT AND TRADEMARK OFFICE
CERTIFICATE OF CORRECTION

PATENT NO.    : 6,287,587 B2
DATED         : September 11, 2001
INVENTOR(S)   : Takada Shigeyuki et al.

It is certified that error appears in the above-identified patent and that said Letters Patent is hereby corrected as shown below:

Column 6,
Line 5, "etc." should read -- etc., --;
Line 18, "etc." should read -- etc., --;
Line 22, "etc.). Said" should read -- etc. The --;
Line 48, "Gly-Asp-Ser)tetramer," should read -- Gly Asp-Ser) tetramer, --; and
Line 51, "andacompoundhaving" should read -- and a compound having --.

Column 8,
Line 37, "2-3];" should read -- 2-3] --; and
Line 52, "Said" should read -- The --.

Column 10,
Line 39, "etc." should read -- etc., --.

Column 11,
Line 6, "polymer" should read -- polymers --;
Line 13, "Said" should read -- The --;
Line 14, "said" should read -- the --;
Line 28, "includes" should read -- include --;
Line 39, "etc." should read -- etc., --; and
Line 41, "etc." should read -- etc., --.

Column 12,
Line 20, "rangespreferablyfrom" should read -- ranges preferably from --;
Line 23, "copolymer(B)" should read -- copolymer (B) --;
Line 40, "KF804L$^x$2" should read -- KF804Lx2 --; and
Line 50, "is used" (first occurrence) should be deleted.

Column 13,
Line 38, "gosaccharides" should read -- gosaccharides, --;
Line 43, "igosaccharides" should read -- gosaccharides, --; and
Line 44, "etc." should read -- etc., --.

Column 14,
Line 20, "etc." should read -- etc., --;
Line 40, "adjustor" should read -- adjustors --;
Line 58, "(hereinafter,briefly" should read -- hereinafter, briefly --;
Line 60, "etc." should read -- etc., --; and
Line 62, "etc." should read -- etc., --.

UNITED STATES PATENT AND TRADEMARK OFFICE
CERTIFICATE OF CORRECTION

PATENT NO. : 6,287,587 B2
DATED : September 11, 2001
INVENTOR(S) : Takada Shigeyuki et al.

It is certified that error appears in the above-identified patent and that said Letters Patent is hereby corrected as shown below:

Column 15,
Lines 4 and 46, "etc." should read -- etc., --;

Column 16,
Lines 20 and 56, "etc." should read -- etc., --; and
Line 37, "W/O=about" should read -- W/O is from about --;

Column 17,
Line 34, "said" should read -- the --; and
Line 45, "etc." should read -- etc., --.

Column 18,
Line 1, "etc." should read -- etc., --;
Line 61, "microcapsule" should read -- microcapsules --; and
Line 67, "are" should read -- is --.

Column 19,
Line 7, "etc." should read -- etc., --
Line 24, "a" (first occurrence) should read -- an --;
Line 31, "etc." (first occurrence) should read -- etc.), --;
Line 52, "etc. to" should read -- etc., to --; and
Line 62, "etc. are" should read -- etc., are --.

Column 20,
Line 23, "exhibits" should read -- exhibit --;
Line 34, "ormore. Sincethe" should read -- or more. Since the --;
Line 55, "mammal" should read -- mammals --.

Column 21,
Line 7, "the.sustained-release" should read -- the sustained-release --.

Column 22,
Line 9, "microcapsule" should read -- microcapsules --;
Line 10, "micorcapsule 20mg was" should read -- microcapsules 20mg were --; and
Line 55, "was" should read -- were --.

UNITED STATES PATENT AND TRADEMARK OFFICE
CERTIFICATE OF CORRECTION

PATENT NO. : 6,287,587 B2
DATED : September 11, 2001
INVENTOR(S) : Takada Shigeyuki et al.

It is certified that error appears in the above-identified patent and that said Letters Patent is hereby corrected as shown below:

Column 23,
Line 3, "was" should read -- were --;
Line 16, "was" should read -- were --;
Line 46, "level" should read -- levels --; and
Line 52, "was" should read -- were --.

Column 24,
Line 38, "hGH/Zn" should read -- Met-hGH/Zn --;
Line 46, "was" should read -- were --;
Line 62, "was" should read -- were --; and
Line 67, "Example 5." should read -- Example 5, --.

Column 25,
Line 22, "(C1 h)" should read -- (C1h) --; and
Line 49, "microcapsle" should read -- microcapsules --.

Column 26,
Line 11, "contains" should read -- contain --;
Line 12, "stable release of" should read -- stably release --;
Line 15, "said" should be deleted;
Line 16, "microcapsules," should read -- microcapsules prepared in this way, --.
Line 40, "polypeptide" should read -- polypeptide, --; and
Line 65, "as" should read -- as a --.

Column 27,
Line 6, "as" should read -- as a --.

Signed and Sealed this

Twenty-third Day of July, 2002

*Attest:*

JAMES E. ROGAN
*Attesting Officer*    *Director of the United States Patent and Trademark Office*